(12) United States Patent
Koh et al.

(10) Patent No.: US 8,603,004 B2
(45) Date of Patent: Dec. 10, 2013

(54) METHODS AND SYSTEMS FOR FILTERING RESPIRATION NOISE FROM LOCALIZATION DATA

(75) Inventors: Steve Koh, South Pasadena, CA (US); Stuart Rosenberg, Castaic, CA (US); Kyungmoo Ryu, Palmdale, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 681 days.

(21) Appl. No.: 12/835,518

(22) Filed: Jul. 13, 2010

(65) Prior Publication Data

US 2012/0016253 A1    Jan. 19, 2012

(51) Int. Cl.
*A61B 5/08*    (2006.01)
*A61B 5/05*    (2006.01)

(52) U.S. Cl.
USPC ............................ 600/534; 600/407; 600/484

(58) Field of Classification Search
USPC .................................................. 600/534, 407
See application file for complete search history.

(56) References Cited

U.S. PATENT DOCUMENTS

| | | | |
|---|---|---|---|
| 5,697,377 A | 12/1997 | Wittkampf | |
| 5,983,126 A | 11/1999 | Wittkampf | |
| 6,640,119 B1 | 10/2003 | Budd et al. | |
| 6,728,562 B1 | 4/2004 | Budd et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,263,397 B2 | 8/2007 | Hauck et al. | |
| 7,885,707 B2 | 2/2011 | Hauck | |
| 2008/0009685 A1* | 1/2008 | Kim et al. | 600/300 |
| 2008/0161681 A1* | 7/2008 | Hauck | 600/424 |
| 2010/0152801 A1 | 6/2010 | Koh et al. | |
| 2010/0317981 A1* | 12/2010 | Grunwald | 600/509 |
| 2011/0118803 A1 | 5/2011 | Hou et al. | |

* cited by examiner

*Primary Examiner* — Michael Kahelin
*Assistant Examiner* — Yunqing Wang
(74) *Attorney, Agent, or Firm* — Wiley Rein LLP

(57) ABSTRACT

A method of filtering respiration noise from a localization signal includes acquiring a localization signal from at least one position measurement sensor within a localization field and acquiring an acceleration signal for at least one localization field generator (e.g., a patch electrode). A displacement signal for the field generator is calculated, for example by integrating the acceleration signal twice, and transformed into the frequency domain in order to calculate a fractional power indicative of patient respiration. The fractional power can then be compared to a threshold value, and the localization signal can be filtered if the fractional power exceeds the threshold value. Alternatively, the acquired acceleration signal can be used to gate collection of data points from the localization signal.

11 Claims, 5 Drawing Sheets

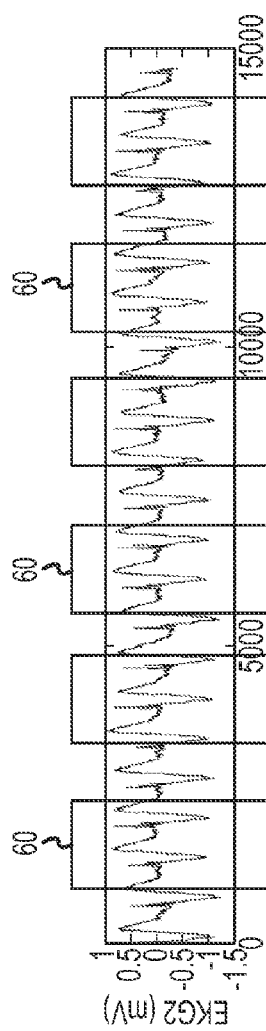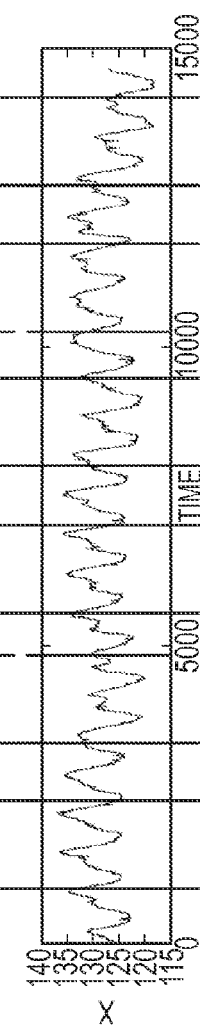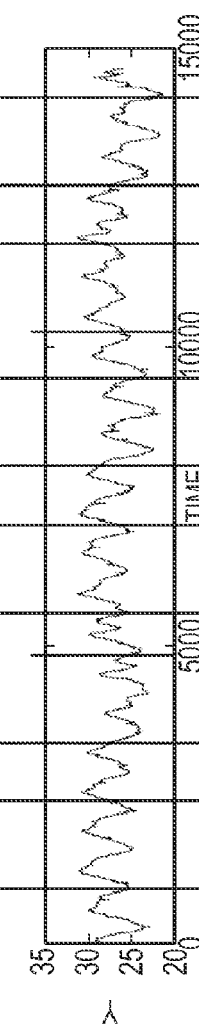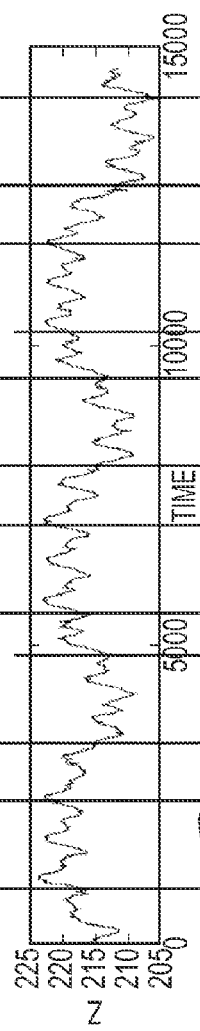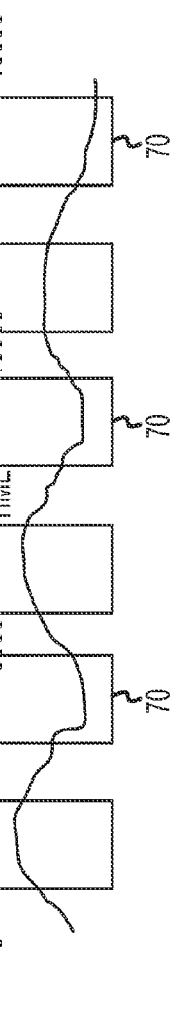

METHODS AND SYSTEMS FOR FILTERING RESPIRATION NOISE FROM LOCALIZATION DATA

BACKGROUND OF THE INVENTION a. Field of the Invention

The instant invention relates to the collection of data regarding a patient, such as geometric data regarding a portion of the patient's anatomy, using a localization system. In particular, the instant invention relates to methods and systems for processing a localization signal that describes the position, and optionally the orientation, of a device within the localization field to account for signal artifacts attributable to patient respiration.

b. Background Art

It is well known how to generate heart chamber geometry in preparation for cardiac diagnostic or therapeutic procedures. Often, a mapping catheter is introduced into the heart chamber of interest and moved around within the heart chamber, either randomly, pseudo-randomly, or according to one or more preset patterns. The three-dimensional coordinates are measured using a localization system (sometimes also referred to as a "mapping system," "navigation system," or "positional feedback system"). The localization system measures the coordinates of the mapping catheter within a localization field, typically by relating a characteristic of the localization field, such as a voltage, experienced by the mapping catheter to a location of the catheter within the field.

Localization signals produced by localization systems often exhibit noise. One prevalent source of noise is patient respiration. Patient respiration may introduce noise by moving the generators and/or references for the localization field or by changing the patient's biological characteristics (e.g., impedance). Thus, an electrode within the localization field that is, in fact, stationary may appear to be moving.

BRIEF SUMMARY OF THE INVENTION

It is desirable to be able to remove the respiration noise component from a localization signal generated by a localization system.

It is also desirable to be able to remove the respiration noise component from a localization signal without attenuating that signal.

Another object of the present invention is to provide a method of collecting localization data that ensures the collected data relates to a common fiducial point within a patient's respiration cycle, such as peak inspiration or peak expiration.

Disclosed herein is a method of filtering a respiration noise component from a localization signal of a localization system. The localization system includes a plurality of localization system patch electrodes that generate a non-ionizing localization field, and at least one of the localization system patch electrodes includes an accelerometer capable of measuring acceleration in at least one direction. The method includes the following steps: acquiring a localization signal of at least one position measurement sensor within the non-ionizing localization field; and acquiring an acceleration signal for the at least one localization system patch electrode; for a selected coordinate axis of the non-ionizing localization field: calculating a displacement signal of the at least one localization system patch electrode on the selected coordinate axis from the acceleration signal; transforming the displacement signal from the time domain into the frequency domain; calculating a fractional power of the transformed displacement signal indicative of patient respiration; comparing the calculated fractional power to a threshold value; and if the calculated fractional power exceeds the threshold value, applying a filter to the localization signal of the at least one position measurement sensor to filter out the respiration noise component on the selected coordinate axis. Optionally, the steps of calculating a displacement signal of the at least one localization system patch electrode on the selected coordinate axis from the acceleration signal, transforming the displacement signal from the time domain into the frequency domain, calculating a fractional power of the transformed displacement signal indicative of patient respiration, comparing the calculated fractional power to a threshold value, and if the calculated fractional power exceeds the threshold value, applying a filter to the localization signal of the at least one position measurement sensor to filter out the respiration noise component on the selected coordinate axis may be repeated for each coordinate axis of the localization field.

In some embodiments of the invention, the step of calculating a fractional power of the transformed displacement signal indicative of patient respiration includes calculating a ratio of an area under the transformed displacement signal between about 0 Hz and about 0.3 Hz to an area under the transformed displacement signal as a whole.

In some embodiments, the at least one localization system patch electrode includes a localization field generator that defines the selected coordinate axis.

The step of calculating a displacement signal of the at least one localization system patch electrode on the selected coordinate axis from the acceleration signal may include: resolving a component of the acceleration signal on the selected coordinate axis; and integrating the component of the acceleration signal on the selected coordinate axis twice.

A Fourier transform may be applied to the displacement signal in order to transform the displacement signal from the time domain into the frequency domain.

Typically, the step of applying a filter to the localization signal of the at least one position measurement sensor to filter out the respiration noise component on the selected coordinate axis includes applying a high-pass filter to the localization signal. Preferably, the cutoff frequency for the high-pass filter is selected to be above the patient's respiration frequency. For example, the threshold value may be selected as the cutoff frequency. Alternatively, the cutoff frequency may be determined using a localization signal acquired from a pseudo-stationary reference electrode positioned within the localization field. In still other embodiments of the invention, the cutoff frequency is determined using the acquired acceleration signal.

The patient's respiration frequency may be identified by: acquiring a displacement signal for at least one pseudo-stationary electrode on at least one coordinate axis of the localization field; transforming the acquired displacement signal from the time domain to the frequency domain; and identifying the patient respiration frequency based upon a low frequency peak of the transformed signal.

In another aspect, the present invention includes a method of filtering a respiration noise component from a localization signal of a localization system that uses a plurality of localization system patch electrodes to generate a non-ionizing localization field, wherein at least one of the patch electrodes includes an accelerometer capable of measuring acceleration in at least one direction. The method includes the following steps: acquiring an acceleration signal for the at least one localization system patch electrode; and gating collection of data points from a localization signal of at least one position measurement sensor within a localization field based upon the acquired acceleration signal.

In some aspects of the invention, the step of gating collection of data points from a localization signal includes: integrating the acquired acceleration signal to calculate a velocity signal and collecting data points from the localization signal only when the calculated velocity signal changes sign from positive to negative. In other aspects of the invention, the gating step includes: integrating the acquired acceleration signal to calculate a velocity signal and collecting data points from the localization signal only when the calculated velocity signal changes sign from negative to positive. In still other aspects of the invention, the step of gating collection of data points from a localization signal includes: integrating the acquired localization signal twice to calculate a displacement signal and collecting data points from the localization signal only when the calculated displacement signal is at a maximum value. In yet further aspects of the invention, the step of gating collection of data points from a localization signal includes: integrating the acquired localization signal twice to calculate a displacement signal and collecting data points from the localization signal only when the calculated displacement signal is at a minimum value.

Also disclosed herein is a localization system for measuring a position of a measurement electrode within a non-ionizing localization field. The localization system includes: a plurality of localization field generators capable of generating a non-ionizing localization field; at least one localization field reference device; at least one accelerometer capable of measuring acceleration in at least one direction coupled to at least one of the plurality of localization field generators and the at least one localization field reference device; and a signal processor that acquires at least one acceleration signal from the at least one accelerometer and that uses the acquired at least one acceleration signal to filter a respiration noise component from a localization signal of at least one position measurement sensor within the non-ionizing localization field.

In certain embodiments of the invention, the signal processor integrates the at least one acceleration signal twice to compute at least one displacement signal and uses the computed at least one displacement signal to filter the respiration noise component from the localization signal. The signal processor may also use a high-pass filter having a cutoff frequency determined using the acquired at least one acceleration signal to process the localization signal. Alternatively, or additionally, the signal processor may process the localization signal by gating collection of data points from the localization signal using the acquired at least one acceleration signal.

An advantage of the present invention is that it permits the filtering of a respiration noise component from a localization signal.

Another advantage of the present invention is that it minimizes attenuation of a localization signal when filtering that signal to remove a respiration noise component.

Still another advantage of the present invention is that it provides a method of collecting localization data at substantially the same point in each respiration cycle.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 3a-3e illustrate the effects of respiration on localization data, wherein:

FIG. 3a is a representative EKG signal;

FIG. 3b is a representative x-axis displacement signal for a localization system patch electrode;

FIG. 3c is a representative y-axis displacement signal for a localization system patch electrode;

FIG. 3d is a representative z-axis displacement signal for a localization system patch electrode; and FIG. 3e is a representative three-dimensional displacement signal for a localization system patch electrode.

FIGS. 5a-5e illustrate a method of filtering a respiration noise component from a localization signal according to another embodiment of the present invention, wherein:

FIG. 5a is a representative EKG signal;

FIG. 5b is a representative x-axis displacement signal for a localization system patch electrode;

FIG. 5c is a representative y-axis displacement signal for a localization system patch electrode;

FIG. 5d is a representative z-axis displacement signal for a localization system patch electrode; and FIG. 5e is a representative three-dimensional acceleration signal for a localization system patch electrode.

DETAILED DESCRIPTION OF THE INVENTION

The present invention provides a method and system for filtering a respiration noise component from a localization signal. As used herein, the term "localization signal" means a signal that describes at least the position, and optionally also the orientation, of a medical device or other object within a localization field. Typically, the localization field will be a non-ionizing localization field, such as an electric or magnetic field.

Such localization fields are often employed in procedures carried out within a human body, and in particular in cardiac diagnostic and therapeutic procedures. Therefore, for purposes of illustration, the invention will be described in detail in the context of a localization system utilized in a cardiac electrophysiology procedure. It is contemplated, however, that the present invention may be practiced to good advantage in other contexts.

Figure 1:
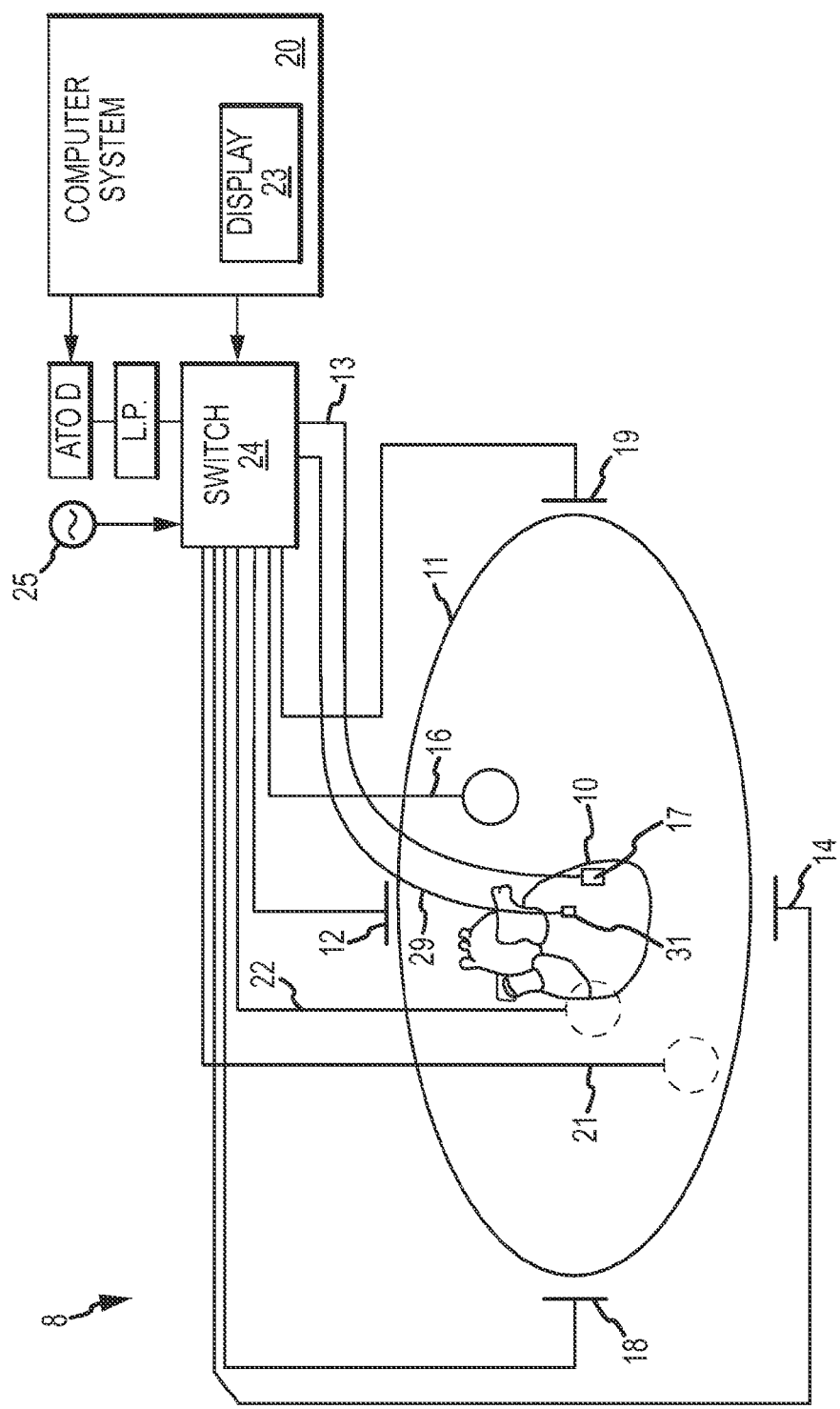
FIG. 1 is a schematic diagram of a localization system utilized in an electrophysiology study.

FIG. 1 shows a schematic diagram of a localization system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface, and store the measured data in association with location information for each measurement point at which the electrophysiology data was measured, for example to create a diagnostic data map of the patient's heart 10. As one of ordinary skill in the art will recognize, and as will be further described below, localization system 8 determines the location of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. Likewise, the electrodes do not need to be on the body surface, but could be fixed on an external apparatus, or electrodes positioned internally to the body could be used.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intracardiac electrode 31, described in further detail below. It should also be appreciated that, in addition, the patient 11 may have most or all of the conventional electrocardiogram ("ECG" or "EKG") system leads in place. This ECG information is available to the system 8, although not illustrated in FIG. 1.

A representative catheter 13 having at least one electrode 17 (e.g., a distal electrode) is also shown. This representative catheter electrode 17 is referred to as the "roving electrode," "moving electrode," "measurement electrode," or "position measurement sensor" throughout this specification. Typically, multiple electrodes on catheter 13, or on multiple such catheters, will be used. In one embodiment, for example, localization system 8 may comprise sixty-four electrodes on twelve catheters disposed within the heart and/or vasculature of the patient. Of course, this embodiment is merely exemplary, and any number of electrodes and catheters may be used within the scope of the present invention.

Figure 2:
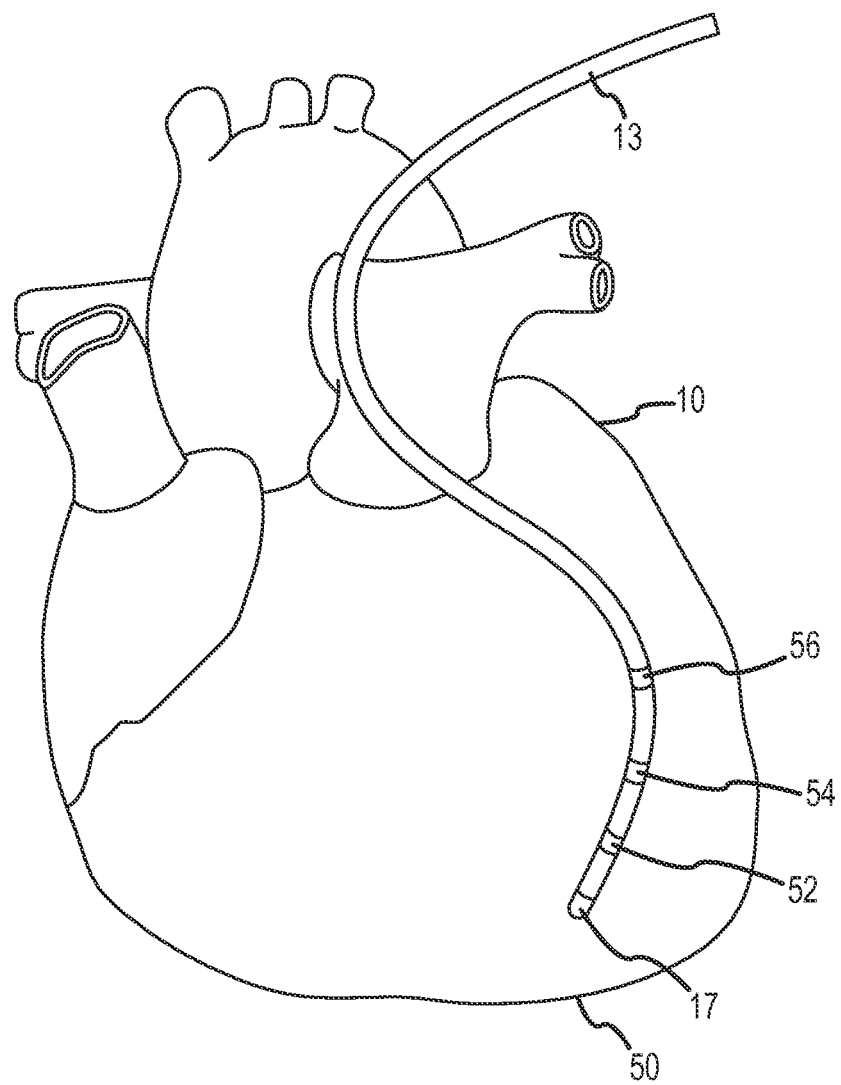
FIG. 2 depicts an exemplary catheter used in an electrophysiology study.

For purposes of this disclosure, an exemplary catheter 13 is shown in FIG. 2. In FIG. 2, catheter 13 extends into the left ventricle 50 of the patient's heart 10. Catheter 13 includes electrode 17 on its distal tip, as well as a plurality of additional position measurement sensors (e.g., measurement electrodes) 52, 54, 56 spaced along its length. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by localization system 8. Thus, each position measurement sensor (e.g., electrodes 17, 52, 54, 56) may generate a localization signal that describes the position, and optionally also the orientation, of catheter 13 within the localization field generated by patch electrodes 12/14, 18/19, and 16/22.

Returning now to FIG. 1, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system for the localization field.

Each surface electrode is coupled to the multiplex switch 24, and the pairs of surface electrodes are selected by software running on a computer 20, which couples the surface electrodes to a signal generator 25. The computer 20, for example, may comprise a conventional general-purpose computer, a special-purpose computer, a distributed computer, or any other type of computer. The computer 20 may comprise one or more processors, such as a single central processing unit (CPU), or a plurality of processing units, commonly referred to as a parallel processing environment, which may execute instructions to practice the various aspects of the present invention described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. For purposes of this disclosure, the invention will be described in connection with a three-dimensional (x, y, z) Cartesian coordinate system. It should be understood, however, that other coordinate systems, such as spherical and cylindrical coordinate systems in three dimensions and polar coordinate systems in two dimensions, are within the scope of the invention.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described in co-pending U.S. application Ser. No. 11/227,580, filed 15 Sep. 2005, which is also incorporated herein by reference in its entirety.

In summary, the system 8 first selects a set of surface electrodes and then drives them with current pulses. While the current pulses are being delivered, electrical activity, such as the voltages measured at least one of the remaining surface electrodes and in vivo electrodes, is measured and stored. Compensation for artifacts, such as respiration and/or impedance shifting, may be performed as indicated above.

In a preferred embodiment, the localization/mapping system is the EnSite NavX™ navigation and visualization system of St. Jude Medical, Atrial Fibrillation Division, Inc., which generates the electrical fields described above. Other localization systems, however, may be used in connection with the present invention, including for example, the CARTO navigation and location system of Biosense Webster, Inc., the AURORA® system of Northern Digital Inc., or Sterotaxis' NIOBE® Magnetic Navigation System, all of which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

The fields generated by localization system 8, whether an electrical field (e.g., EnSite NavX™), a magnetic field (e.g., CARTO, AURORA®, NIOBE®), or another suitable field, may be referred to generically as "localization fields," while the elements generating the fields, such as surface electrodes 12, 14, 16, 18, 19, and 22 may be generically referred to as "localization field generators." As described above, surface electrodes 12, 14, 16, 18, 19, and 22 may also function as detectors to measure the characteristics of the localization field (e.g., the voltages measured at roving electrodes 17, 52, 54, 56, or a current from roving electrodes 17, 52, 54, 56), and thus may also be referred to as "localization elements." Though the present invention will be described primarily in the context of a localization system that generates an electrical field, one of ordinary skill in the art will understand how to apply the principles disclosed herein in other types of localization fields, and in particular other types of non-ionizing localization fields (e.g., by replacing electrodes 17, 52, 54, 56 with coils to detect different components of a magnetic field).

The basic localization methodology described above provides a first order indication of the location of a roving or other catheter electrode within the heart chamber. As one of ordinary skill in the art will appreciate, however, the localization signal may include artifacts (e.g., a noise component) attributable to patient respiration. For example, when measured with reference to the belly patch 21, displacement errors exceeding two centimeters have been noted in the left atrium in data measured with a roving catheter electrode 17. When referenced to a fixed electrode, such as intracardiac electrode 31, the measured displacement error still exceeded about one centimeter. That is, patient respiration may cause roving electrodes 17, 52, 54, and 56 to appear to be as far as 2 cm away from their actual location in the three-dimensional space of the localization field.

These errors may be caused by several different aspects of patient respiration. First, when the lungs fill with air, the current paths from the localization field generators change. This alteration of current path changes the measured potential between roving electrode 17 and the reference electrode (e.g., belly patch 31). Respiration also moves the localization system patch electrodes (e.g., localization field generators 12/14, 18/19, 16/22 and belly patch 31); this displacement may also change the apparent position of an object within the localization field. The resistivity of blood returning to the heart from the lungs is also altered following inspiration. Full lungs may also have a compressive effect on the heart that may cause displacement of the catheter itself.

Figure 3A:
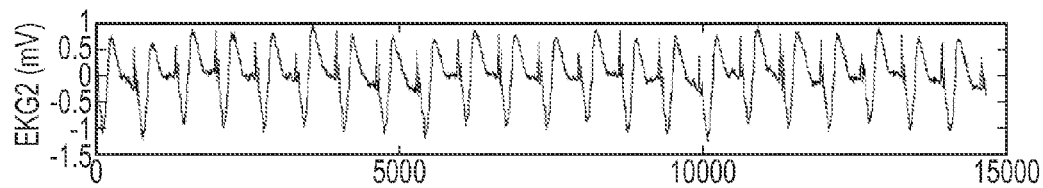
Figure 3B:
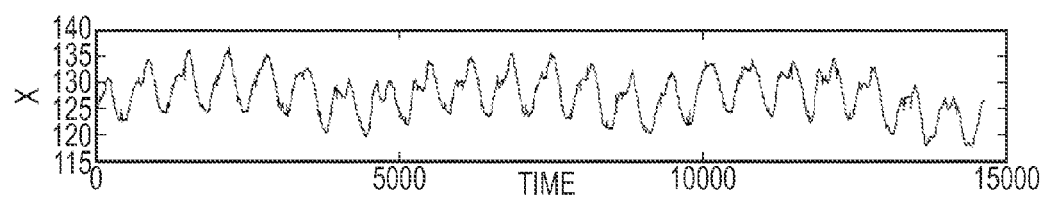
Figure 3C:
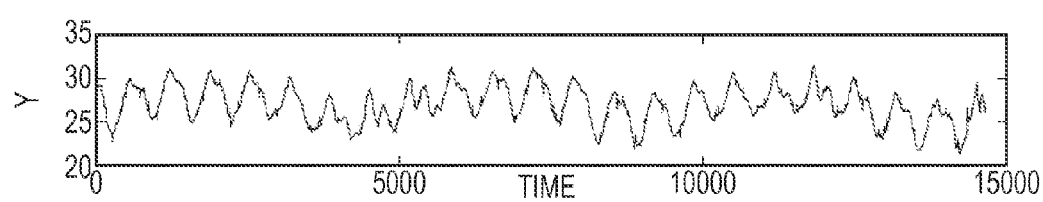
Figure 3D:
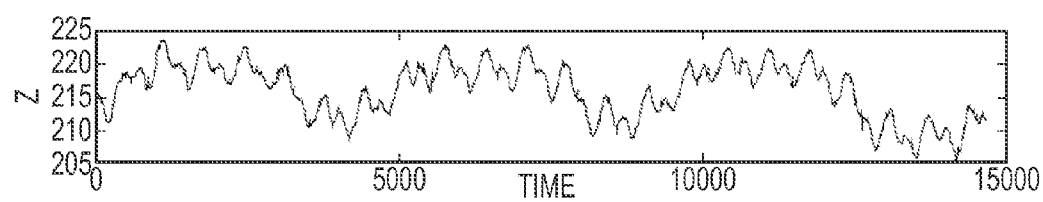
Figure 3E:
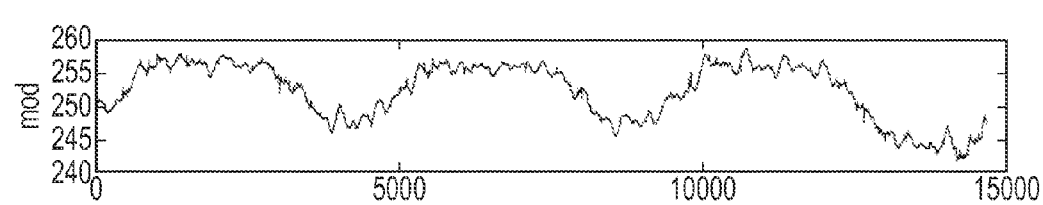

This potential for error in the localization signal will be apparent to one of ordinary skill in the art from reviewing FIGS. 3*a-e*, which show the movement of a localization field generator for the z-axis (e.g., patch electrode 16 or 22) on the x, y, and z-axes (FIGS. 3*b*, 3*c*, and 3*d*, respectively), as well as in three dimensions (FIG. 3*e*). For the sake of understanding, the movement of the patch electrode is juxtaposed with the signal received by an EKG lead (FIG. 3*a*). As will be understood from FIGS. 3*b*-3*d*, this electrode exhibits considerable respiration noise on the z-axis (FIG. 3*d*), and much less respiration noise on the x-axis (FIG. 3*b*) and y-axis (FIG. 3*c*).

As noted above, U.S. Pat. No. 7,263,397 discloses a method of compensating for these respiration artifacts. As an alternative or in addition to this respiration compensation methodology, the present invention provides methods to filter a respiratory noise component from a localization signal acquired from a position measurement sensor (e.g., one or more of electrodes 17, 52, 54, and 56).

The present invention employs accelerometers attached to one or more of the localization system patch electrodes (e.g., localization field generators 12/14, 18/19, and 16/22, as well as belly patch 21) in order to acquire a signal that describes the motion of the patch electrodes. Preferably, each of the localization system patch electrodes is equipped with an accelerometer, but the invention could be practiced in a localization system where fewer than all of the patch electrodes includes an accelerometer. It is also desirable for the accelerometers to be capable of measuring acceleration in three dimensions, though the invention could still be practiced with accelerometers having more limited capabilities.

Figure 4:
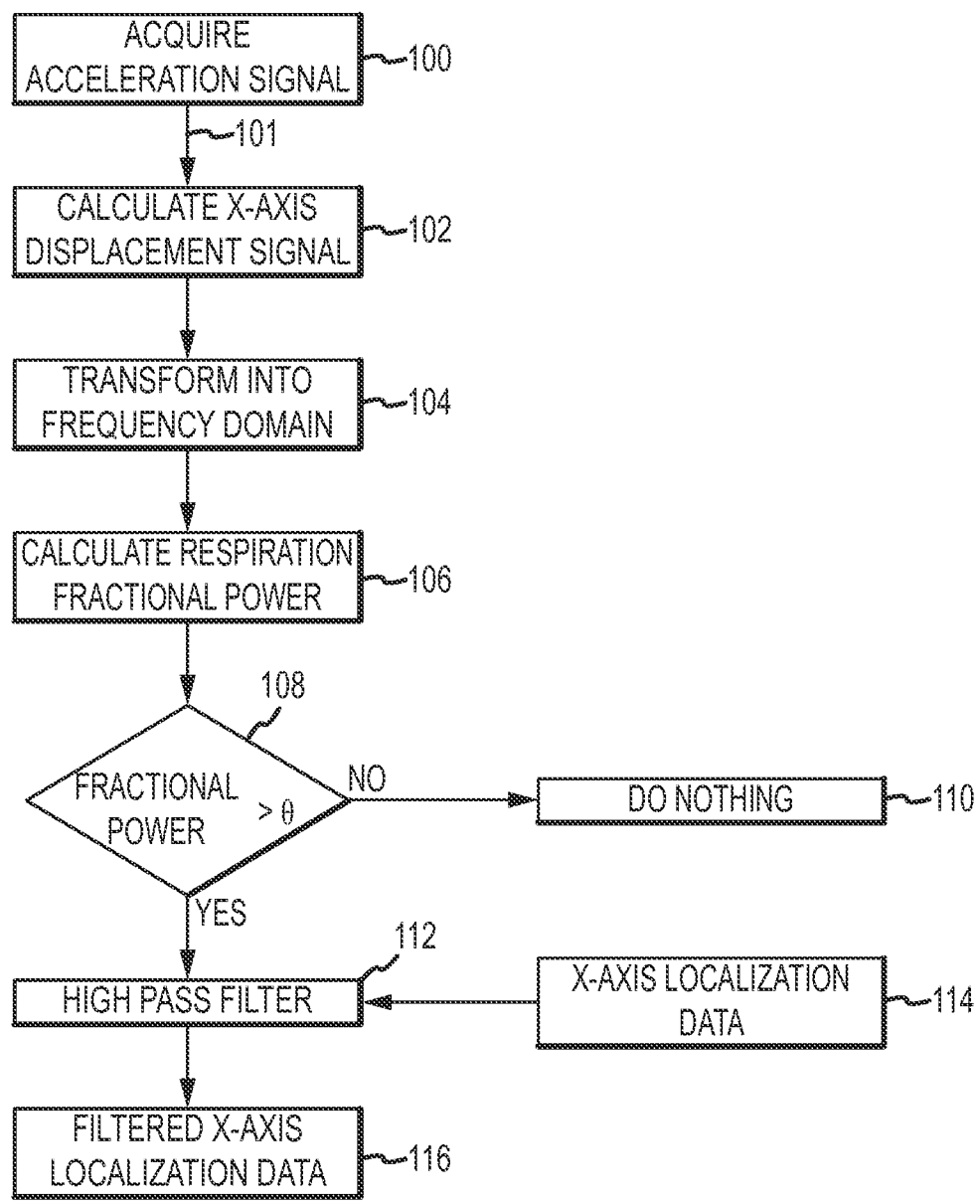
FIG. 4 is a flowchart of a method of filtering a respiration noise component from a localization signal according to an embodiment of the present invention.

A first method of filtering a respiration noise component from a localization signal will be described with reference to the flowchart of FIG. 4. FIG. 4 illustrates application of this method according to the present invention in order to filter a respiration noise component from the x-axis component of a localization signal acquired from a position measurement sensor, such as electrode 17, within the localization field. One of ordinary skill in the art will appreciate how to extend the method of FIG. 4, as described herein, to other coordinate axes defining the localization field.

In block 100, an acceleration signal is acquired for at least one patch electrode. Preferably, the acceleration signal is acquired for at least one patch electrode that defines the coordinate axis on which the respiration noise component is to be filtered (e.g., the acceleration signal from patch electrodes 12 and/or 14 will be used to filter on the x-axis; the acceleration signal from patch electrodes 18 and/or 19 will be used to filter on the y-axis; and the acceleration signal from patch electrodes 16 and/or 22 will be used to filter on the z-axis).

In block 102, the acquired acceleration signal is used to calculate a displacement signal of the at least one patch electrode on the x-axis. That is, the acquired acceleration signal is processed in order to generate a signal that describes the movement of the at least one patch electrode. Thus, in moving from block 100 to block 102, the acquired acceleration signal is integrated twice and resolved into vector components along the x, y, and z-axes (line 101). Of course, the acquired acceleration signal may be resolved into its components either prior to or after double integration.

Once the x-axis displacement signal has been calculated, it is transformed from the time domain into the frequency domain in block 104. This may be accomplished, for example, by applying a Fourier transform to the x-axis displacement signal. The transformed signal will typically exhibit two peaks: a low frequency peak resulting from the respiration noise component, and a high frequency peak resulting from the physiological component.

In block 106, a fractional power of the transformed signal attributable to patient respiration is calculated. This may be accomplished by calculating a ratio of two integrals of the transformed x-axis displacement signal: the integral of the transformed x-axis displacement signal between about 0 Hz and about 0.3 Hz (a range sufficient to cover most, if not all, respiratory activity), and the integral of the transformed x-axis displacement signal as a whole.

In decision block 108, the fractional power of the transformed signal attributable to patient respiration is compared to a threshold value θ, discussed in further detail below. If the fractional power is less than the threshold value, then there is not a significant respiration noise component on the x-axis, and no further action needs to be taken (block 110).

If, on the other hand, the fractional power exceeds the threshold value, then there is a significant respiration noise component on the x-axis, and it would be desirable to filter this component out of the x-axis component of the localization signal. Preferably, this is accomplished by applying a high-pass filter (block 112) to the x-axis component of the localization signal (block 114), thereby outputting a filtered x-axis component of the localization signal (block 116). A high-pass filter is used in order to filter out the relatively low frequency respiration noise component while preserving the relatively high frequency physiological component. Thus, the cutoff frequency of the high-pass filter should be set above the patient's respiratory frequency but below the frequency of the physiological signal.

The threshold value θ will typically be selected on an individualized basis for each patient. Preferably, θ is computed using patch electrode displacement data for a localization system coordinate axis that does not exhibit significant respiratory noise (referred to herein as a "quiet" axis). For example, FIGS. 3b and 3c show that the depicted patch electrode is experiencing very little respiratory noise on the x- and y-axes. Therefore, either the x- or y-axis could be used to determine a suitable θ. Typically, θ will be computed by transforming the displacement signal for the quiet axis into the frequency domain and selecting a value that falls above the lower frequency peak of the respiration noise signal and below the higher frequency peak of the physiological signal. As a matter of convenience, this same value may also be used as the cutoff frequency for the high pass filter.

It should be understood that the threshold value, cutoff frequency, and/or patient's respiration frequency may be determined using any pseudo-stationary reference electrode. As used herein, the term "pseudo-stationary" refers to an electrode that is not intended to be moving, although it may appear to be moving due to external influences. Thus, patch electrodes 12/14, 18/19, 16/22, and 21, as well as fixed intracardiac electrode 31, are all considered pseudo-stationary—they are supposed to remain stationary to provide a fixed frame of reference for the localization system. Electrodes 17, 52, 54, and 56, however, are not pseudo-stationary, as they are intended to move through the patient's heart.

Thus, in some embodiments of the invention, a localization signal of intracardiac electrode 31 is used to determine the threshold value, cutoff frequency, and/or patient's respiration frequency. Of course, because this is a localization signal, it already represents displacement and need not be integrated before being transformed into the frequency domain.

In other embodiments of the invention, an acceleration signal from a patch electrode is used to determine the threshold value, cutoff frequency, and/or patient's respiration frequency. This signal may need to be integrated twice to compute a displacement signal prior to further processing.

Another embodiment of the present invention will now be described with reference to FIGS. 5a-5e. In this embodiment of the invention, the collection of localization data is gated to the patient's respiratory cycle, using the acquired acceleration signal, such that all data is collected at the same fiducial point in each respiration cycle (e.g., data is always collected at peak inspiration or always collected at peak expiration).

FIGS. 5b-5d depict, respectively, patch electrode motion on the x-, y-, and z-axes. FIG. 5e is the acceleration signal for the patch electrode. For the sake of comparison, FIGS. 5b-5e are shown juxtaposed with an EKG signal (FIG. 5a). Throughout, the darker shaded bands 60 represent patient inspiration, while the lighter shaded bands 70 represent patient expiration.

There are many ways in which data collection may be gated. In some aspects of the invention, the acquired acceleration signal is integrated once to yield a velocity signal, and data points are collected only when the velocity signal on all coordinate axes changes sign. For example, when the velocity signals change sign from positive to negative, it corresponds to peak inspiration, when the patient begins to exhale. Conversely, when the velocity signals change sign from negative to positive, it corresponds to peak expiration, when the patient begins to inhale.

In other aspects of the invention, the acquired acceleration signal is integrated twice to yield a displacement signal, and data points are collected only when the displacement signal on all coordinate axes is at an extreme. For example, when the displacement signals are at their maxima, it corresponds to peak inspiration, when the patient begins to exhale. Conversely, when the displacement signals are at their minima, it corresponds to peak expiration, when the patient beings to inhale.

By gating the collection of data points as described above, a "fair playing field" is ensured. It should be understood that, although data points are collected on a gated basis (i.e., at the same fiducial point in each respiration cycle), the localization signal may nonetheless be constantly tracked. That is, the location of electrodes 17, 52, 54, and 56 may be monitored in real time, but only stored according to the patient's respiratory signal.

The methods described above may be executed by one or more computer systems (e.g., computer system 20), and may be software implemented (e.g., one or more software programs executed by one or more computer systems or processors), hardware implemented (e.g., a series of instructions stored in one or more solid state devices), or a combination of both. The computer may be a conventional general purpose computer, a special purpose computer, a distributed computer, or any other type of computer. Further, the computer may comprise one or more processors, such as a single central processing unit or a plurality of processing units, commonly referred to as a parallel processing environment. The term "processor" as used herein refers to a computer microprocessor and/or a software program (e.g., a software module or separate program) that is designed to be executed by one or more microprocessors running on one or more computer systems.

For example, a localization system for measuring a position of a measurement electrode within a non-ionizing localization field may include: a plurality of localization field generators capable of generating a non-ionizing localization field (e.g., patch electrodes 12/14, 18/19, and 16/22); at least one localization field reference (e.g., belly patch 21 and/or intracardiac electrode 31); at least one accelerometer that is capable of measuring acceleration in at least one direction coupled to at least one of the plurality of localization field generators and the at least one localization field reference; and a signal processor that acquires at least one acceleration signal from the at least one accelerometer and uses that acquired acceleration signal to filter a respiration noise component from a localization signal received from at least one position measurement sensor (e.g., electrodes 17, 52, 54, and 56) within the localization field.

The methods disclosed herein can be employed to good advantage in various contexts, including cardiac therapeutic contexts. For example, it has been proposed to use various vector-based metrics, such as the variation in distance between electrodes in various heart chambers, in connection with cardiac pacing and cardiac resynchronization therapy, such as disclosed in U.S. application Ser. Nos. 12/621,373, filed 18 Nov. 2009, and 12/621,397, filed 18 Nov. 2009, and U.S. provisional application No. 61/121,737, filed 11 Dec. 2008, all of which are hereby incorporated by reference as though fully set forth herein. The present teachings can aid in minimizing the effect of respiratory oscillations in determining these desirable vector-based metrics.

Although several embodiments of this invention have been described above with a certain degree of particularity, those skilled in the art could make numerous alterations to the disclosed embodiments without departing from the spirit or scope of this invention. For example, rather than transforming the displacement signal from the time domain into the frequency domain, a slow-moving average filter may be applied to the displacement signal in order to smooth out the cardiac component and determine the peak-to-peak interval. The peak-to-peak interval will, in turn, facilitate determination of the respiration cycle, which can be used to determine the appropriate cutoff frequency for the filter (e.g., a high-pass filter).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of filtering a respiration noise component from a localization signal of a localization system including a plurality of external localization system patch electrodes that generate a non-ionizing localization field, the method comprising:

acquiring a localization signal of at least one position measurement sensor within the non-ionizing localization field; and acquiring an acceleration signal from at least one of the localization system patch electrodes, the at least one localization system patch electrode comprising an accelerometer capable of measuring acceleration in at least one direction;

for a selected coordinate axis of the non-ionizing localization field:

calculating a displacement signal of the at least one localization system patch electrode on the selected coordinate axis from the acceleration signal;

transforming the displacement signal from the time domain into the frequency domain;

calculating a fractional power of the transformed displacement signal indicative of patient respiration;

comparing the calculated fractional power to a threshold value; and when the calculated fractional power exceeds the threshold value, applying a filter to the localization signal of the at least one position measurement sensor to filter out the respiration noise component on the selected coordinate axis.

2. The method according to claim 1, wherein the step of calculating a fractional power of the transformed displacement signal indicative of patient respiration comprises calculating a ratio of an area under the transformed displacement signal between about 0 Hz and about 0.3 Hz to an area under the transformed displacement signal as a whole.

3. The method according to claim 1, further comprising repeating the steps of:

calculating a displacement signal of the at least one localization system patch electrode on the selected coordinate axis from the acceleration signal;

transforming the displacement signal from the time domain into the frequency domain;

calculating a fractional power of the transformed displacement signal indicative of patient respiration;

comparing the calculated fractional power to a threshold value; and when the calculated fractional power exceeds the threshold value, applying a filter to the localization signal of the at least one position measurement sensor to filter out the respiration noise component on the selected coordinate axis for each coordinate axis of the localization field.

4. The method according to claim 1, wherein the at least one localization system patch electrode comprises a localization field generator that defines the selected coordinate axis.

5. The method according to claim 1, wherein the step of calculating a displacement signal of the at least one localization system patch electrode on the selected coordinate axis from the acceleration signal comprises:

resolving a component of the acceleration signal on the selected coordinate axis; and integrating the component of the acceleration signal on the selected coordinate axis twice.

6. The method according to claim 1, wherein the step of transforming the displacement signal from the time domain into the frequency domain comprises applying a Fourier transform to the displacement signal.

7. The method according to claim 1, wherein the step of applying a filter to the localization signal of the at least one position measurement sensor to filter out the respiration noise component on the selected coordinate axis comprises applying a high-pass filter to the localization signal, wherein a cutoff frequency for the high-pass filter is selected to be above a patient respiration frequency.

8. The method according to claim 7, wherein the threshold value is selected as the cutoff frequency.

9. The method according to claim 7, wherein the cutoff frequency is determined using a localization signal acquired from a pseudo-stationary reference electrode positioned within the localization field.

10. The method according to claim 7, wherein the cutoff frequency is determined using the acquired acceleration signal.

11. The method according to claim 7, wherein the patient respiration frequency is identified by:
- acquiring a displacement signal for at least one pseudo-stationary electrode on at least one coordinate axis of the localization field;
- transforming the acquired displacement signal from the time domain to the frequency domain; and
- identifying the patient respiration frequency based upon a low frequency peak of the transformed signal.

* * * * *